United States Patent
van Andel et al.

(10) Patent No.: US 6,291,992 B1
(45) Date of Patent: *Sep. 18, 2001

(54) EDDY CURRENT INSPECTION TECHNIQUE

(75) Inventors: Petrus Willem van Andel; Maarten Lorenz; Ricky Eduardo Ricardo Meyer, all of Amsterdam (NL)

(73) Assignee: Shell Oil Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,989

(22) Filed: Jun. 30, 1997

(30) Foreign Application Priority Data

Dec. 7, 1996 (EP) .................................................. 96201978

(51) Int. Cl.[7] .......................... G01N 27/82; G01N 27/90; G01N 7/06
(52) U.S. Cl. ......................... 324/240; 324/242; 324/230
(58) Field of Search ................................... 324/240, 239, 324/238, 242, 220, 227, 229, 230

(56) References Cited

U.S. PATENT DOCUMENTS

| | | | |
|---|---|---|---|
| 3,315,155 | 4/1967 | Colani | 324/40 |
| 3,532,969 | 10/1970 | McCullough et al. | 324/34 |
| 3,707,672 | 12/1972 | Miller et al. | 324/239 |
| 3,940,689 | * 2/1976 | Johnson, Jr. | 324/37 |
| 4,107,605 | * 8/1978 | Hudgell | 324/238 |
| 4,271,393 | * 6/1981 | Hansen et al. | 324/240 |
| 4,418,574 | 12/1983 | Flournoy | 73/601 |
| 4,553,095 | * 11/1985 | Schenk, Jr. et al. | 324/230 |
| 4,629,985 | 12/1986 | Papadimitriou et al. | 324/232 |
| 4,710,712 | 12/1987 | Bradfield et al. | 324/227 |
| 4,717,006 | 1/1988 | Chapman et al. | 194/318 |
| 4,839,593 | * 6/1989 | Spies | 324/240 |
| 4,843,319 | * 6/1989 | Lara | 324/240 |
| 4,843,320 | * 6/1989 | Spies | 324/240 |
| 4,929,896 | * 5/1990 | Lara | 324/240 |
| 4,929,898 | * 5/1990 | Spies | 324/229 |
| 4,990,851 | * 2/1991 | Spies | 324/240 |
| 5,059,902 | 10/1991 | Linder | 324/207.17 |
| 5,233,297 | * 8/1993 | Lara | 324/240 |
| 5,434,506 | * 7/1995 | Flora | 324/242 |
| 5,446,382 | * 8/1995 | Flora | 324/242 X |
| 5,461,313 | * 10/1995 | Bohon et al. | 324/240 |

FOREIGN PATENT DOCUMENTS 8604315   10/1986 (SE) .

OTHER PUBLICATIONS

W. E. Deeds and C. V. Dodd, "Determination of Multiple Properities Eddy–Current Measurements," *International Advances in Nondestructive Testing*, 1981 vol. 8, pp. 317–333.

"A Pulsed Eddy Current Technique for Measureing Clad thickness", by D. L. Waidelich et al., ANL–5614, pp, 1–49*

"The Response to Pulsed Eddy Currents of a Metal Plate", by D. L. Waidelich, University of Missouri–Columbia, pp. 23–34.*

* cited by examiner

Primary Examiner—Safet Metjahic
Assistant Examiner—T. R. Sundaram

(57) ABSTRACT

A device is disclosed for inspecting an object of electrically conductive material, in which a non-static-signal transmitter generates an electromagnetic field in the object, and a receiver measures the variations of the eddy current generated by the non-static electromagnetic field and produces a signal representing the decay of the eddy current. The non-static-signal transmitter is provided with at least two laterally spaced-apart emitters for emitting an electromagnetic field, which emitters are, during normal operation, so driven that the resulting electromagnetic field in the central region between the emitters is intensified.

21 Claims, 4 Drawing Sheets

EDDY CURRENT INSPECTION TECHNIQUE

BACKGROUND OF THE INVENTION

The present invention relates to inspecting an object of electrically conductive material. In the specification and in the claims the phrase "inspecting an object" is used to refer to operations such as measuring the thickness of the object, checking the object for the presence of sub-surface flaws and measuring the thickness of a layer of non-conductive material around the object. The object can be, for example, a wall of a container or the wall of a pipe.

The effective thickness of an object, for example, a wall of a steel container, a pipe or a vessel can be locally affected by external or internal corrosion. In case the object is provided with a layer of insulation material, corrosion detection by visual inspection generally implies temporary removal of the insulation material, which is time consuming and expensive.

U.S. Pat. No. 4,843,320 issued Jun. 27, 1989 to B. R. Spies discloses a device for measuring a thickness of an object of electrically conductive material, such as a wall, comprising a pulsed-signal transmitter for generating an electromagnetic field in the wall and a receiver for measuring the decay of the eddy current generated by the electromagnetic field and for producing a signal representing the decay.

To determine the thickness of the wall, the decay of the received signal over a period of time is compared with the decay of a reference signal indicative of a known wall thickness.

The transmitter includes an emitter coil and the receiver includes a receiver coil. The coils are wound around a core, and, during normal operation, the central longitudinal axis of the core is perpendicular to a surface of the object.

With the known device, corrosion spots of a size comparable to that of the emitter coil can be detected, however, it was found that spots which are relatively small compared to the coil size cannot be detected. Such small corrosion spots, however, can locally reduce the wall thickness to a significant extent. Furthermore, the size of such a small spot can rapidly grow, for example when liquid water is present between the pipe and an insulation layer surrounding the pipe.

It is an advantage of the invention to provide a device which provides an enhanced resolution so as to allow a more detailed inspection of the object.

It is another advantage of the invention to provide an improved method of interpreting measured data to determine wall thickness.

SUMMARY OF THE INVENTION

To this end the device for inspecting an object of electrically conductive material according to the present invention comprises a non-static-signal transmitter for generating an electromagnetic field in the object, and a receiver for measuring the variations of the eddy current generated by the non-static electromagnetic field and for producing a signal representing the decay of the eddy current, wherein the non-static-signal transmitter comprises at least two laterally spaced-apart emitters for emitting an electromagnetic field, which emitters are, during normal operation, so driven that the resulting electromagnetic field in the central region, between the emitters, is intensified.

By intensifying the electromagnetic field in the central region, an eddy current of increased density can be generated in a small selected wall portion, and in this way the eddy current is focused in this selected wall portion. The eddy current receiver means can be arranged so as to measure the decay of the eddy current of increased density without measuring the decay of eddy currents of lower density, i.e. outside the selected wall portion. In this way a better resolution is achieved.

The central region is located between the emitters, and suitably it is located between the centers of the emitters.

In accordance with another aspect of the invention there is provided a method of measuring a thickness of an object of electrically conductive material, which method according to the invention comprises inducing a pulsed eddy current in the object, determining the decay of the eddy current and producing a signal representing the decay, and determining the thickness of the object from the signal, wherein the step of determining the thickness of the object from the signal comprises selecting a first magnitude and a second, smaller magnitude of the amplitude of the signal, measuring the length of the time interval in which the signal decays from the first magnitude to the second magnitude, and determining the thickness of the object from the length of the time interval.

A BRIEF DESCRIPTION OF THE DRAWINGS

The brief description above, as well as further objects and advantages of the present invention, will be more fully appreciated by reference to the following detailed description of the preferred embodiments which should be read in conjunction with the accompanying drawings in which:

FIG. 1 schematically shows a perspective view of an embodiment of the device according to the invention;

Figure 4:
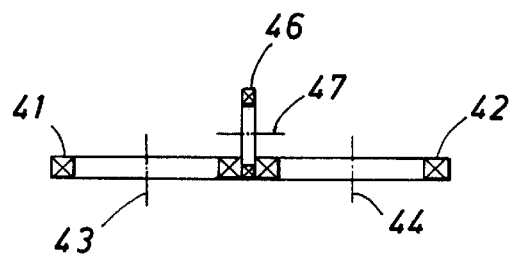
Figure 5:
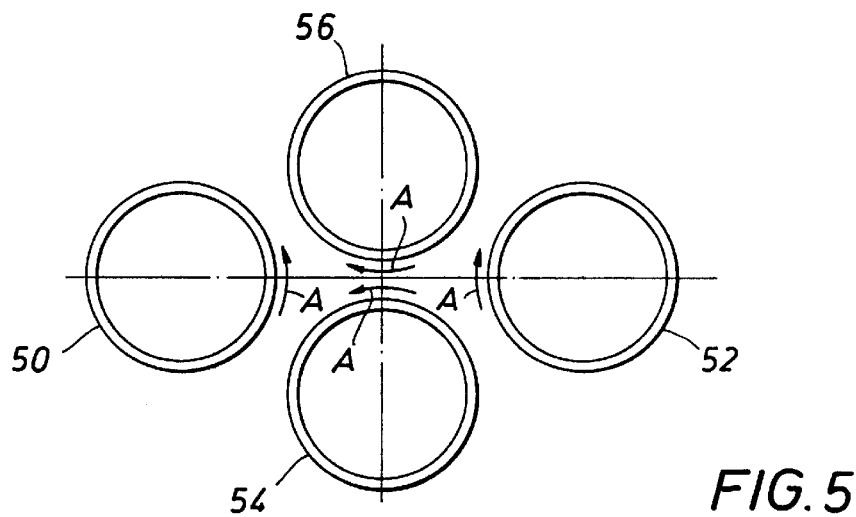
Figure 6:
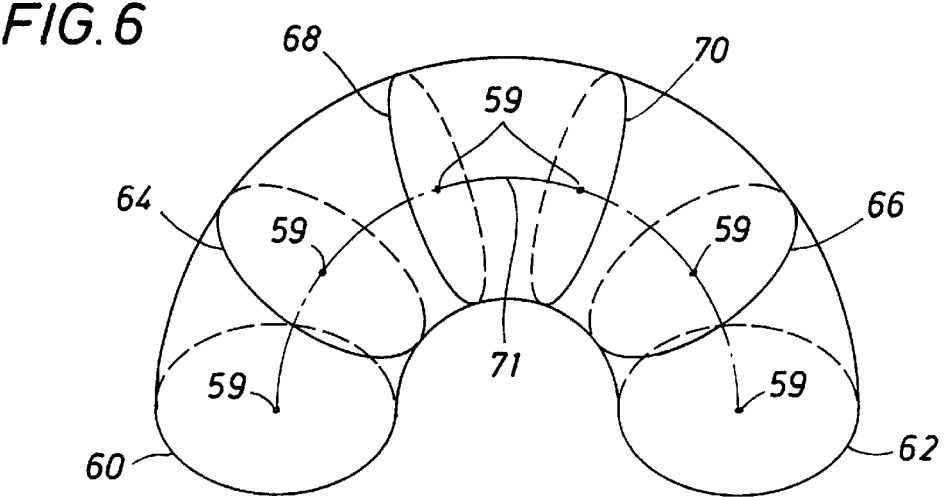
Figure 7:
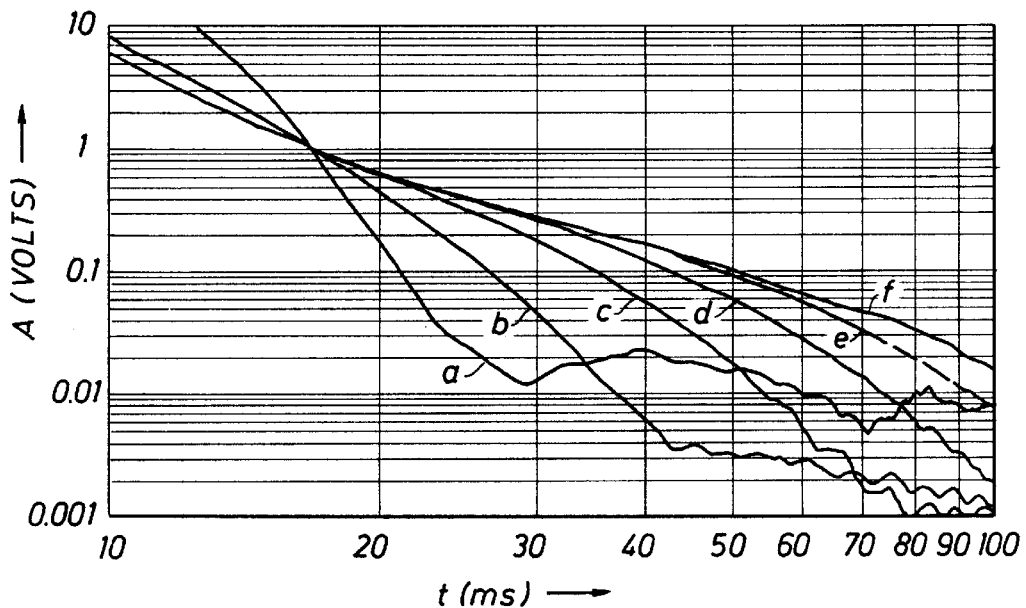
Figure 8:
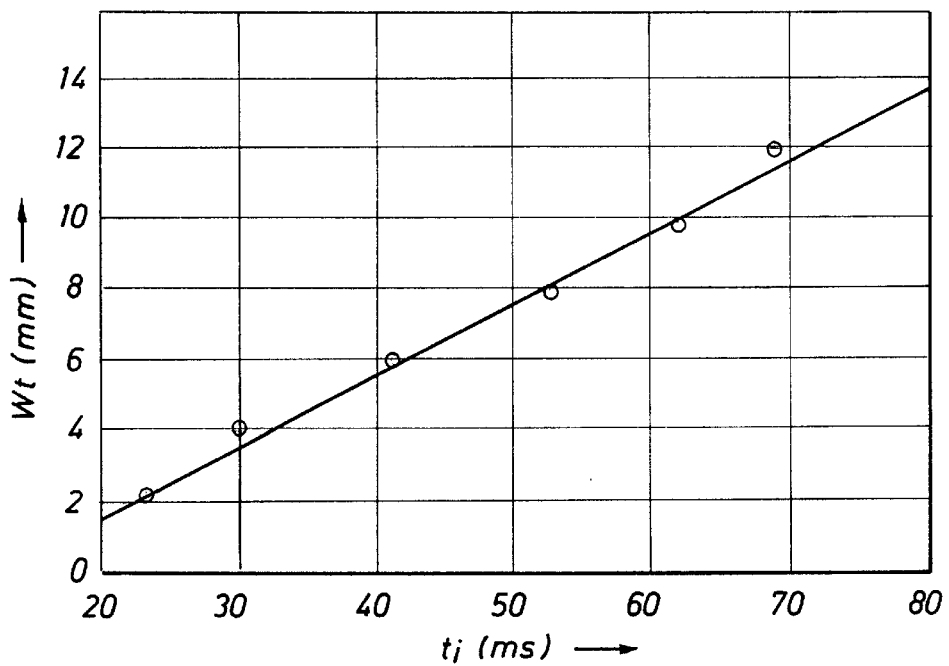
Figure 9:
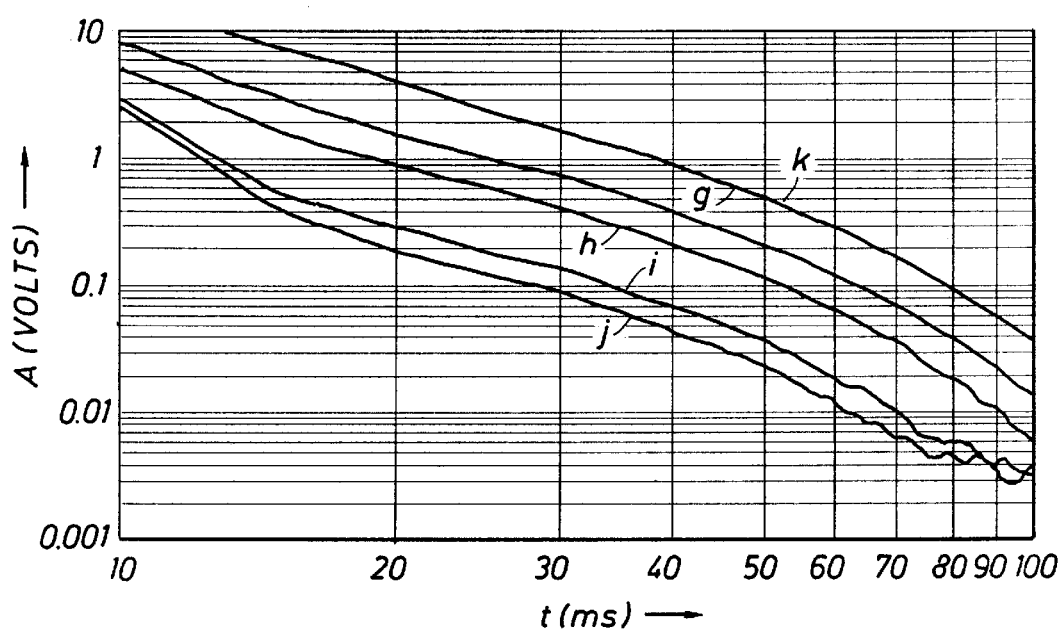

FIG. 4 schematically shows an alternative embodiment of the device according to the invention;

FIG. 5 schematically shows yet another embodiment of the device according to the invention;

FIG. 6 schematically shows a further embodiment of the device according to the invention;

FIG. 7 shows eddy current decay curves in a double-logarithmic diagram;

FIG. 8 shows a linear calibration curve applied to determine wall thickness; and FIG. 9 shows the effect of a spacing between probe and wall on the decay curves in a double-logarithmic diagram.

A DETAILED DESCRIPTION OF ILLUSTRATIVE EMBODIMENTS

In the following description, like reference numerals relate to like components.

Figure 1:
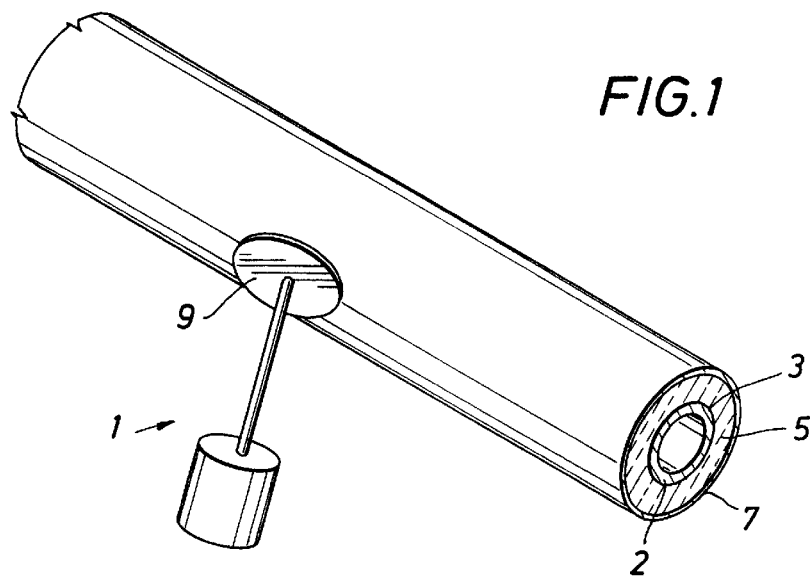

Reference is now made to FIG. 1 which shows a probe 1 for inspecting an object of electrically conductive material, such as for measuring the thickness of a wall 2 of a pipe 3 in order to detect the presence of corrosion at the wall 2. The corrosion can be located at the outer or inner surface of the wall 2. A layer 5 of insulating material enclosed by a thin metal steel jacket 7 surrounding the layer 5 of insulating material is provided around the pipe 3. The probe 1 includes a device 9 for inspecting an object of electrically conductive material, which during normal operation, is held against the outer surface of the steel jacket 7.

Figure 3:
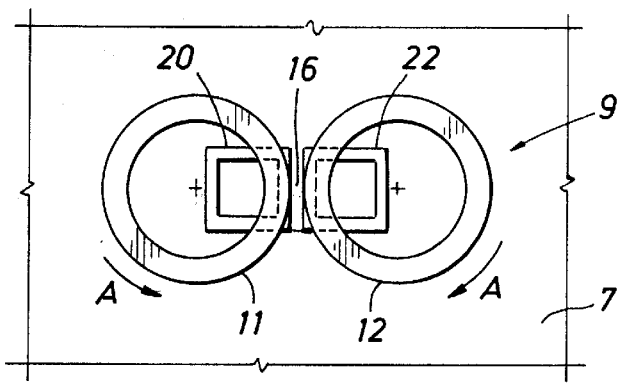
FIG. 3 shows a top view of the part shown in FIG. 2.
Figure 2:
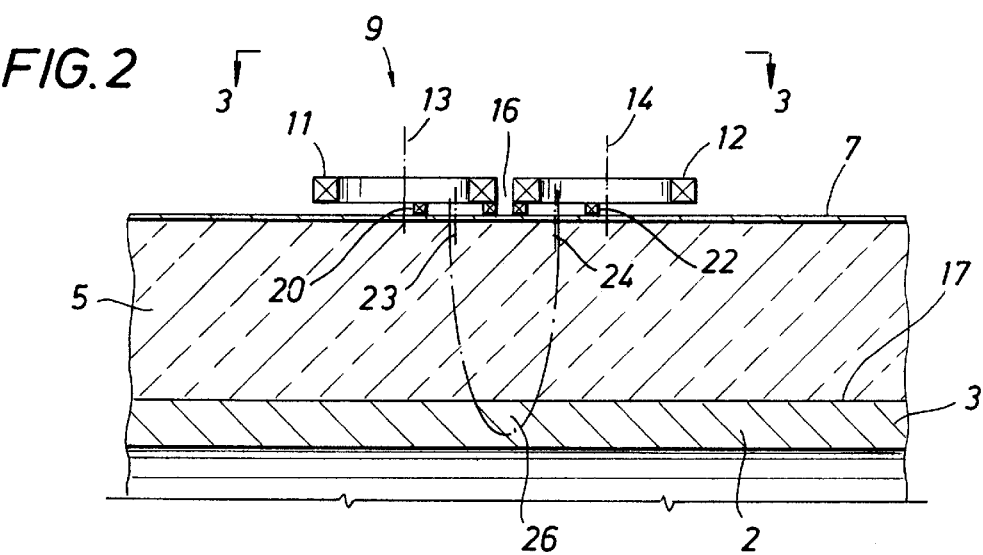
FIG. 2 shows a transverse cross-section of a part of the device of FIG. 1 drawn to a larger scale.

Reference is now made to FIGS. 2 and 3, the device 9 for inspecting the object of electrically conductive material comprises a non-static-signal transmitter (not shown) for generating a non-static electromagnetic field in the object in the form of the wall 2 and a receiver (not shown) for measuring the variations of the eddy current generated by the non-static electromagnetic field and for producing a signal representing the decay of the eddy current.

The non-static-signal transmitter comprises at least two laterally spaced-apart emitters for emitting an electromagnetic field, in the form of a first emitter coil 11 and a second emitter coil 12, which are spaced apart in a direction lateral to the direction of their central longitudinal axes 13 and 14, respectively. Between the emitter coils 11 and 12 there is a relatively small gap 16. During normal operation the emitter coils are arranged parallel to a near surface 17 of the object in the form of the wall 2, so that their central longitudinal axes 13 and 14 are perpendicular to the near surface 17.

The transmitter further includes means (not shown) which drive the emitters in the form of emitter coils 11 and 12.

The receiver includes at least one receiver coil arranged to receive the electromagnetic field generated by the eddy current in the object in the form of the wall 2, in the form of a first receiver coil 20 and a second receiver coil 22, having central longitudinal axis 23 and 24, respectively. The receiver coils 20 and 22 are identical, and have a square cross-section. They are arranged substantially parallel to the near surface 17 of the object in the form of the wall 2. The pair of receiver coils 20, 22 is arranged aligned with the corresponding pair of emitter coils 11, 12, that is to say the central longitudinal axes 13 and 14, and 23 and 24 of the coils are substantially parallel to each other and extend in the same plane (that is the plane of drawing of FIG. 2). The size of the receiver coils 20 and 22 is smaller than the size of the emitter coils 11 and 12 and the central longitudinal axes 23 and 24 of the receiver coils 20 and 22 extend between the central longitudinal axes 13 and 14 of the emitter coils 11 and 12. The voltage over the terminals of the receiver coils is the signal representing the decay of the eddy current in the object.

During normal operation, the emitters in the form of emitter coils 11 and 12 are so driven that the resulting electromagnetic field in the central region, between the centers 25 of the emitters 11 and 12, is intensified. The central region is indicated with reference numeral 26. This is done by passing a current through each of the emitter coils 11 and 12 such that the direction of the currents in the emitter coils is not the same. In FIG. 3 the direction of the currents is indicated by arrows arrows I. As a result, the electromagnetic field in the central region 26 is intensified, that is to say it is stronger in a region between the emitter coils 11 and 12 and weaker outside the central region 26. Consequently in the object 2 there is a region 27 where the density of the electromagnetic is larger than outside that region 27. Hereinbelow the region 27 of increased density of the electromagnetic field will be called the detection region 27. In this way a better resolution is achieved and relatively small corrosion spots can be detected.

To improve reception, the receiver coils 20 and 22 are in connected in series and they are located at opposite sides of the gap 16 and of the detection region 27.

Suitably the diameter of each emitter coil 11 and 12 is substantially equal to the thickness of the insulation layer 5. For example, for an insulation thickness of 70 mm, two emitter coils of 200 windings of 0.5 mm wire having a diameter of 70 mm are used.

The gap 16 overlays the detection region 27 of the wall 2 of the pipe 3 which is to be checked for corrosion.

In FIG. 4 is shown an alternative embodiment wherein the arrangement of emitter coils 41 and 42 is similar to the arrangement of emitter coils 11 and 12 shown in FIGS. 2 and 3. However, instead of two receiver coils being arranged in a plane parallel to that of the emitter coils, only one receiver coil 46 is provided. The receiver coil 46 is located between the emitter coils 41 and 42 and its central longitudinal axis 47 extends perpendicular to the central longitudinal axes 43 and 44 of the emitter coils 41 and 42.

Reference is now made to FIG. 5 showing another arrangement of coils including a first pair of emitter coils 50 and 52 and a second pair of emitter coils 54 and 56, the pairs being disposed substantially co-planar and in close proximity to each other. The arrow I indicates the directions of the electric currents in the emitter coils 50, 52, 54 and 56. The first pair of emitter coils 50 and 52 on one hand and the second pair of emitter coils 54 and 56 on the other hand induce eddy currents of increased density in different directions in the selected wall portion between the emitter coils 50, 52, 54 and 56. In the embodiment shown the eddy currents of increased density flow in mutually perpendicular directions. Each pair of emitter coils is provided with a corresponding pair of receiver coils (not shown), the receiver coils of each pair being of the same type and being arranged in the same manner with respect to the corresponding emitter coils as with reference to FIG. 3. This embodiment has the advantage over the embodiment of FIG. 3 that the device is even better focused on the wall portion of interest, and that the measurement is more symmetrical. Instead of two pairs of coils, any other suitable number of pairs of coils may be applied in an analogous way.

Reference is now made to FIG. 6 and an alternative embodiment of the invention showing an emitter coil array. The coil array is shown having the emitter coils 60, 62, 64, 66, 68, and 70 arrayed along a semicircular arc 71, the arc having an origin 71a and terminus 71b. The arc 71 is shown as passing through the center 59 of each emitter coil such that the arc 71 is perpendicular to the plane of the coil as it passes through the center 59 of the respective coils 60, 62, 64, 66, 68, and 70. FIG. 6 depicts the coil array as being arranged within a non-conducting conduit or body 73 used to support the coils. It will be appreciated that the emitter coils 60, 62, 64, 66, 68, and 70 need not be carried or supported by a conduit or body 73. Moreover, it will be further appreciated the coils may be arranged such that the plane of each coil is perpendicular to arc 71 as it passes through the each coil's center 59 (not shown).

In a further alternative embodiment, a semi-circular bar of ferromagnetic material (not shown) is arranged within the emitter coils.

The essence of the present invention is that the laterally spaced apart emitters are so driven that the resulting electromagnetic field in the central region, between the emitters, is intensified. In the above this effect has been described with two or four or six emitter coils, however, it has been found that the same effect can be achieved with only one emitter coil. To achieve the same effect, the laterally spaced-apart emitters comprise a coil substantially parallel to a near surface of the object and a bar of ferromagnetic material substantially perpendicular to the near surface of the object. In an alternative embodiment, the laterally spaced-apart emitters consist of an emitter coil in the form of an 8-shaped figure substantially parallel to a near surface of the object.

Reference is now made to FIG. 2. A suitable non-static signal is a pulse. During normal operation of the probe 1 pulsed electric currents are induced to flow in the emitter coils 11 and 12 in opposite rotational directions. A constant current flows through the emitter coils 11 and 12 during each pulse time T. The current and its associated electromagnetic field are switched on and off at respectively the rising and falling edge of the pulse. The emitter coils 11 and 12 are sufficiently large that at least some of the electromagnetic field lines penetrate through the jacket 7, the insulating layer 5 and the wall 2 of the steel pipe 3. The electromagnetic field lines in the wall 2 will mainly be concentrated in the vicinity of the near surface 17. An electromagnetic flux change occurs when the electromagnetic field is switched on or off, which flux change induces an eddy current in the wall 2 of the pipe 3 near the external surface 7. The eddy currents resulting from the separate emitter coils 11 and 12 flow in opposite rotational directions in the wall 2, so that an eddy current of increased density results in the detection region 27 of the wall 2 of the pipe 3 below the gap 16. The generated eddy currents diffuse through the wall 2 and are reflected by the internal surface of the wall 2 back to the external surface 17. The pulse duration T is selected to be longer than the typical diffusion time to ensure that a step response is measured. The pulse duration range is typically between 50 and 300 ms, depending on the thickness of the wall 2 of the pipe 3.

A pulsed eddy current will diffuse in the depth direction (i.e. towards the internal surface) and in the radial direction with respect to its own loop (i.e. outwards so as to increase the eddy current loop radius). Furthermore, a charge transport along the eddy current loop takes place. The diffusion velocity is approximately 100 times higher than the velocity of charge transport along the eddy current loop. This implies that an eddy current can diffuse through the wall 2 and reflect from the internal surface with only a minor charge displacement along the loop. The diffusion within the detection region 27 is therefore largely independent on the diffusion and current flow outside the detection region 27. This makes it possible to take measurements that are only sensitive for a fraction of the eddy current. Suitably the electronics, the emitter and receiver coils for fractional pulsed eddy current measurement are designed such that impedance changes do not influence the measurement.

The receiver coils 20 and 22 are of smaller size than the emitter coils 11 and 12 so that the receiver coils 20 and 22 are only sensitive for field lines of eddy currents flowing in the detection region 27. The windings sense of the receiver coils 20 and 22 is such that an absolute probe for the eddy current field lines is created, i.e. the currents induced in the receiver coils 20 and 22 by the field lines enhance each other. At the same time a differential probe for noise (50/60 Hz) is created, i.e. the currents induced in the receiver coils by noise cancel each other. Typically the rectangular receiver coils 20 and 22 have a size of 30 mm by 30 mm by 2 mm, and have 100 windings of 0.1 mm wire.

Normal use of the alternative embodiment of FIGS. 4, 5 and 6 is similar to normal use of the device described with reference to FIGS. 1 through 3.

The signal representing the decay of the eddy currents is the voltage over the receiver coils, of which the amplitude V (volts) is evaluated as a function of the time after the current and the associated electromagnetic field has been switched off at the fall of the pulse. FIG. 7 shows a double-logarithmic diagram wherein the amplitudes V of six eddy current decay curves are plotted against the time t (in ms, milliseconds). The eddy current decays are obtained by applying a suitable eddy current probe to steel container walls of different thicknesses. The curves a, b, c, d, e and f show the decay for walls having a thickness of respectively 2, 4, 6, 8, 10 and 12 mm. The initial parts of the curves approach straight lines in the double-logarithmic diagram. Applicant has found that there is a linear relationship between the wall thickness and the time elapsed for the eddy current to decay from a first value to a second value, for example from 1 V to 0.05 V. This linear relationship is used in the present invention to measure the thickness of an unknown wall.

The curves of FIG. 7 are used to determine the constants in the linear relationship. To this end the wall thickness is plotted as a function of the time elapsed for the eddy current to decay from 1 V to 0.05 V, and this is shown in FIG. 8.

In FIG. 8 is shown the substantially linear relationship between the wall thickness $W_t$ (in mm) and the time $t_i$ (in ms) elapsed until the curves of FIG. 7 have decayed from 1 V to a selected magnitude of 0.05 V. The indicated dots correspond to the measurements pertaining to curves a, b, c, d, e, f of FIG. 7. The relationship is $W_t=(t_i-A)/B$, in which A and B are calibration constants which are determined from the linear calibration curve of FIG. 8.

The eddy current probe can be calibrated by adjusting the magnitude of A so as to compensate for variations in permeability, temperature and wall curvature. A single measurement at a location with a known wall thickness is sufficient to find the magnitude of A. Small fluctuations in the magnitude of B may result in deviations in the wall thickness readings of approximately 10% (or approximately 1 mm). Such accuracy is sufficient for detection of corrosion under a layer of insulating material.

Reference is now made to FIG. 9. It has been found that at least after an initial period of time after the end of the last transmitter current pulse the effect of a spacing between the eddy current receiver means and the wall of electrically conductive material, for example due to lift-off or a layer of insulating material, is a vertical shift of the curve in the double-logarithmic diagram. This effect is shown in FIG. 8 for measurement on a 8 mm thick steel plate provided with a 1 mm aluminum jacket and an insulating layer between the steel plate and the aluminum jacket, the insulating layer having a thickness of respectively 20, 40, 80 and 100 mm for curves g, h, i and j. Curve k relates to a measurement on the steel plate without insulating layer or jacket.

The spacing is taken into account in the measurement by vertically shifting the curve in the double-logarithmic diagram in a manner that the amplitude of the signal has its first magnitude, for example 1 V, at a selected time such as between 10 and 20 ms, preferably 15 ms, after the end of a transmitter current pulse. By taking into account the spacing in this manner the signal decay curves have a common intersection point. This is for example shown in FIG. 7 in which the signal decay curves have been vertically shifted so as to have their common intersection point at time=15 ms after the end of the last pulse.

The effect of the aluminum jacket surrounding the insulation layer is a change in amplitude and a retardation of the signal when the electromagnetic field penetrates the jacket. Amplitude changes do not affect the wall thickness measurement because they are compensated for by the amplitude measurement which is used to set the intersection point of the curves (at 15 ms in above example). Signal retardation occurs due to diffusion of eddy currents generated in the jacket. However retardation is only a few milliseconds, depending on the jacket material, and the slope of the signal decay curve is hardly affected by the presence of the jacket. The retardation can be compensated for by adjusting the magnitude of B, for example by ensuring that during calibration a jacket is present. Other influences of the jacket, for example due to overlaps, dents or screws, all occur at relatively early times, i.e. before 15 ms after the end of the last pulse. Therefore these influences do not affect wall thickness measurements for which the time interval of measurement starts after 15 ms after the end of the last pulse.

The device and method according to the invention can be applied to objects of electrically conductive material of various structures, such as for example the wall of a pipe provided with insulation layers or the wall of a storage tank. In case the bottom wall of a large storage tank (e.g. for oil storage) is to be inspected, the device according to the invention can for example be held against the lower side of the bottom by first excavating a substantially horizontal hole in the ground below the tank and subsequently moving the device through the borehole and against the bottom of the tank.

Furthermore, the device and method of the invention are of particular interest for application on vessels, pipes and plates which are provided with a layer of non-conducting material, such as bitumen or epoxy resin. The coating hinders inspection by conventional techniques (e.g. ultra sound or visual). Also applications involving extremely high or low temperatures of a wall to be inspected, which preclude the application of conventional techniques requiring direct contact with the wall, are of interest since no direct contact of such a wall with the probe used in the present invention is required.

Other modifications, changes, and substitutions are also intended in the forgoing disclosure. Further, in some instances, some features of the present invention will be employed without a corresponding use of other features described in these illustrative embodiments. Accordingly, it is appropriate that the appended claims be construed broadly and in a manner consistent with the spirit and scope of the invention herein.

What is claimed is:

1. A device for inspecting an object of electrically conductive material, comprising:
   a signal transmitter for generating an electromagnetic field in the object, inducing eddy currents in the object during operation of the transmitter;
   a receiver for measuring the decay of the eddy current following operation of the transmitter and for producing a signal representing the decay of the eddy current; and
   a processor for determining the thickness of the object as a linear function of the eddy current decay signal;
   wherein the signal transmitter comprises a signal generator connected to at least two emitters coils, the emitter coils being substantially co-planar and in close proximity to each other, for emitting the electromagnetic field, which emitters coils are, during normal operation, so driven that the resulting electromagnetic field in a central region, between the emitters, is intensified.

2. The device according to claim 1, wherein the plane of the emitter coils is located proximate to and substantially parallel to a near surface of the object.

3. The device according to claim 1, comprising a plurality of of emitter coils, the emitter coils being substantially co-planar and in close proximity to one another.

4. The device according to claim 1, wherein the emitter coils are wound about a ferromagnetic core.

5. The device according to claim 1, wherein the emitter coils consist of a single emitter coil in the form of an 8-shaped figure, the plane of the figure being substantially parallel to a near surface of the object.

6. The device according to any one of claim 1, wherein the receiver includes at least one receiver coil arranged to receive the electromagnetic field generated by the eddy current in the object.

7. The device according to claim 6, wherein the receiver includes a co-planar first receiver coil and a second receiver coil in close proximity to the central region in a plane substantially parallel to a near surface of the object.

8. The device according to claim 7, wherein each receiver coil is in close proximity to an emitter coil.

9. The device according to claim 6, wherein each receiver coil is located between the emitter coils and the object.

10. A method of measuring a thickness of an object of electrically conductive material, the method comprising:
    inducing a pulsed eddy current in the object;
    determining the decay of the eddy current and producing a signal representing the decay; and
    determining the thickness of the object from the signal;
    wherein the step of determining the thickness of the object from the signal comprises:
    selecting a first magnitude and a second, smaller magnitude of the amplitude of the signal;
    measuring the length of the time interval in which the signal decays from the first magnitude to the second magnitude; and
    determining the thickness of the object as a linear function of the time interval.

11. The method according to claim 10, wherein the thickness ($W_t$) is determined from the
    length of the time interval ($t_i$) with the following equation:

$$W_t = (t_i - A)/B,$$

in which A and B are predetermined calibration constants.

12. An apparatus for inspecting an electrically conductive object, comprising:
    (a) a transmitter connected to at least two emitter coils, the emitter coils being substantially co-planar and in close proximity to each other, the transmitter inducing eddy currents in the object during operation;
    (b) a receiver for detecting the decay of the eddy currents following operation of the transmitter and producing a signal representative of the decay of the eddy currents; and
    (c) a processor for determining the thickness of the object as a linear function of the eddy current decay signal.

13. The apparatus of claim 12, wherein the emitter coils are disposed in a plane substantially parallel to a near surface of the object.

14. The apparatus of claim 13, wherein the emitter coils are wound about a ferromagnetic core.

15. The apparatus of claim 12, wherein the receiver is comprised of at least one receiver coil, the receiver coil being in close proximity to the emitter coils.

16. The apparatus of claim 12, wherein the receiver is comprised of at least two receiver coils, the receiver coils being substantially co-planar and in close proximity to each other.

17. The apparatus of claim 16, wherein the receiver coils are disposed in close proximity to the emitter coils and in a plane substantially parallel to a near surface of the object.

18. An apparatus for determining the thickness of an electrically conductive object, comprising:
    (a) a transmitter connected to a coil array, the coil array being comprised of at least three emitter coils disposed in a semicircular arc, the origin and terminus of the arc being substantially perpendicular to a near surface of the object, the plane of the coils for each emitter coil being substantially perpendicular to the arc, the transmitter inducing eddy currents in the object during operation;

(b) a receiver for detecting the decay of the eddy currents in the object following operation of the transmitter and producing a signal representative of the eddy current decay; and (c) a processor for determining the thickness of the object as a linear function of the eddy current decay signal.

19. The apparatus of claim 18, wherein the receiver is comprised of at least one receiver coil, the receiver coil being disposed substantially parallel to the near surface of the object and between the origin and terminus of the coil array.

20. The apparatus of claim 19, wherein the receiver is comprised of at least two receiver coil, the receiver coils being substantially co-planar and in close proximity to each other.

21. The apparatus of claim 18, wherein each emitter coil is wound about a ferromagnetic core.

* * * * *